(12) United States Patent
Park et al.

(10) Patent No.: US 7,365,509 B2
(45) Date of Patent: Apr. 29, 2008

(54) CAPSULE TYPE MICRO-ROBOT MOVING SYSTEM

(75) Inventors: Suk-Ho Park, Seoul (KR); Byung-Kyu Kim, Seoul (KR); Hyun-Jun Park, Gyeonggi-Do (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 11/431,354

(22) Filed: May 10, 2006

(65) Prior Publication Data

US 2006/0257234 A1 Nov. 16, 2006

(30) Foreign Application Priority Data

May 12, 2005 (KR) .................... 10-2005-0039884

(51) Int. Cl.
*A61B 1/00* (2006.01)
(52) U.S. Cl. .................. 318/568.12; 600/101; 900/1
(58) Field of Classification Search ........... 318/568.11, 318/568.12; 901/1; 600/101, 109, 112, 600/114

See application file for complete search history.

(56) References Cited

U.S. PATENT DOCUMENTS

| | | | | |
|---|---|---|---|---|
| 5,337,732 A | * | 8/1994 | Grundfest et al. .......... 600/116 |
| 5,662,587 A | * | 9/1997 | Grundfest et al. .......... 600/114 |
| 6,240,312 B1 | * | 5/2001 | Alfano et al. ............... 600/476 |
| 6,520,272 B2 | * | 2/2003 | Cho et al. .................... 180/8.1 |
| 6,719,684 B2 | * | 4/2004 | Kim et al. ................... 600/101 |
| 6,737,160 B1 | | 5/2004 | Full et al. ................... 428/397 |
| 6,824,508 B2 | * | 11/2004 | Kim et al. ................... 600/101 |
| 6,824,510 B2 | * | 11/2004 | Kim et al. ................... 600/114 |
| 6,911,004 B2 | * | 6/2005 | Kim et al. ................... 600/101 |

FOREIGN PATENT DOCUMENTS

KR 10-2002-0088681 11/2002

\* cited by examiner

*Primary Examiner*—Bentsu Ro
(74) *Attorney, Agent, or Firm*—Ostrolenk, Faber, Gerb & Soffen, LLP

(57) ABSTRACT

A capsule type micro-robot moving system moves on an organ's wall covered with mucilage at a high speed. The present invention provides a capsule type micro-robot moving system, which is structured such that a head is formed in a semi-spherical shape and the outer surface of the capsule is coated with an anti-adhesion coating agent for reducing friction against organs during the movement, particularly, is structured to move as long as a linear stroke corresponding to the distance between the driving part and the inner cylinder in the state that the limbs folded in and unfolded out of the capsule completely contact and stick to the walls of the organs, resulting in providing the reliability and moving more rapidly.

25 Claims, 14 Drawing Sheets

CAPSULE TYPE MICRO-ROBOT MOVING SYSTEM

CROSS-REFERENCE TO RELATED APPLICATIONS

This application claims the benefit of Korean Patent Application No. 2005-39884, filed on May 12, 2005, in the Korean Intellectual Property Office, the disclosure of which is incorporated herein by reference.

BACKGROUND

1. Field of the Invention

The present invention relates to a capsule type micro-robot moving system, and more particularly, to a capsule type micro-robot moving system capable of moving at a high speed while holding a mucilage wall of an internal organ.

2. Discussion of Related Art

Generally, a micro-robot utilized in a capsule type endoscope includes a subminiature camera for capturing the inside of an internal organ, tweezers for tearing off a tissue of the internal organ, a communication unit for transmitting an image captured by the camera to an external device, and a diagnosing equipment, and is used to inspect a diseased part like a medical doctor touches the tissue of the internal organ. As such, by using the micro-robot, the inside of the internal organ such as the stomach, the small intestine, the large intestine, or the like can be captured by the endoscope without giving a patient pains, and a simple surgical operation and the injection of medical drug can be performed.

However, a conventional micro-robot for a capsule type endoscope does not commercialized till now and its research is being developed. As one of robot moving systems, it is in progress a research for an inchworm type micro-robot moving system treading with clamping part expanded by air and stepping the wall of the large intestine. However, in order to move the micro-robot using this principle, it must be required a close contact between a body of the micro-robot and the surrounding on which the micro-robot will move. However, since the wall of the organ is coated with mucilage and has a viscoelastic property, there is a limit in the close contact.

SUMMARY OF THE INVENTION

The present invention has been made in view of the above and/or other problems, and it is an objective of the present invention to provide a capsule type micro-robot moving system capable of moving at a high speed even in an organ coated with slippery mucilage and giving reliability.

In order to achieve the above objectives and another aspect of the present invention, the present invention provides a capsule type micro-robot moving system including: an inner cylinder having a locking groove formed in the outer circumference thereof; a driving part for moving the inner cylinder in the longitudinal direction; an outer cylinder having a hollow part formed therein to surround the inner cylinder; a first exposing hole penetrating the outer circumference of the outer cylinder in the longitudinal direction; the limb hinged to the outer cylinder to rotate by a predetermined range, exposed over the first exposing hole when the limb is unfolded due to the rotation, and hided in the first exposing hole when the limb is folded due to the rotation; a capsule for surrounding the outer cylinder; and a second exposing hole aligned with the first exposing hole and formed in the longitudinal direction of the capsule such that the limb is exposed over the capsule when the limb is unfolded; wherein the limb is folded or unfolded when the limb interferes with the locking groove in the movement direction of the inner cylinder.

Preferably, the outer cylinder has hinge recess formed continuously in the circumferential direction, rotation center holes are formed in the rotation centers of the limbs, and a wire is inserted into the rotation center hole in the outer cylinder and the rotation center hold of limbs and is placed in the hinge recess.

Moreover, the capsule type micro-robot moving system further includes a rotation prevention recess formed in the outer circumference of the outer cylinder, and a rotation prevention protrusion formed in the inner circumference of the capsule to be engaged with the rotation prevention recess. On the contrary, the capsule type micro-robot moving system may further include a rotation prevention protrusion formed in the outer circumference of the outer cylinder, and a rotation prevention recess formed in the inner circumference of the capsule to be engaged with the rotation prevention recess.

The inner cylinder has a hollow part penetrating the central portion thereof, the inner cylinder has a groove formed in the outer circumference of the inner cylinder in the longitudinal direction to prevent the inner cylinder from rotating within the outer cylinder, the outer cylinder has a protrusion formed in the inner circumference of the outer cylinder and engaged with the groove, and the driving part includes a motor installed to the rear side of the capsule, and a screw rod rotated in association with the rotation of the motor and fastened in the hollow part of the inner cylinder.

On the contrary, the capsule type micro-robot moving system may further include: a guide hole penetrating the inner cylinder in the longitudinal direction; and a guide rod penetrating and fixed in the guide hole; wherein the driving part includes a motor installed to the rear side of the capsule, and a screw rod rotated in association with the rotation of the motor and fastened in the hollow part of the inner cylinder.

Preferably, the capsule type micro-robot moving system further includes a camera installed in a head of the capsule.

In order to decrease friction between the wall of the organ and the capsule, a head of the capsule in which the camera is installed has a semi-spherical shape, and the capsule is preferably coated with an anti-adhesion agent for reducing friction against the organ during the movement.

The limb has three or more limbs for the effective contact with the wall of the organ and the limbs are arranged in the radial direction.

Preferably, in order to increase friction between the limbs advancing while holding the wall of the organ and the wall of the organ, a plurality of minute protrusions is formed in the ends of the limbs. Here, the minute protrusions are formed in the form of minute cilium to increase adhesive force between the ends of the limbs and the wall of the organ. Due to this structure different from a mechanical movement of sharpen ends of the limbs holding the wall of the organ, damages of the wall of the organ that would be occurred during the movement can be remarkably reduced and the capsule type robot can softly hold the wall of the organ and move. In addition, in order for the ends of the limbs having the minute cilia to easily contact and be separated from the wall of the organ, flexible joints may be formed in the ends of the limbs.

The driving part may include a PZT linear ultrasonic motor. In this case, by using the PZT linear ultrasonic motor, the movement of the inner cylinder in the longitudinal direction can be achieved.

In order to transmit images captured by the camera of the capsule to the exterior unit, preferably, a communication unit for transmitting the images of the gastrointestinal tract to the exterior receiver is further included.

When the above locking recesses are formed in the outer circumference of the inner cylinder in series in the circumferential direction, the capsule type micro-robot moving system is easily fabricated.

Moreover, the above locking recesses are vertically caved to form a flat bottom so that the locking between the locking groove and the limbs is maximized.

BRIEF DESCRIPTION OF THE DRAWINGS

These and/or other objects and advantages of the invention will become apparent and more readily appreciated from the following description of preferred embodiments, taken in conjunction with the accompanying drawings of which:

FIGS. 1 to 6 are views illustrating a capsule type micro-robot moving system according to a first preferred embodiment of the present invention, in which:

FIG. 1 is an exploded perspective view illustrating a capsule type micro-robot moving system;

FIG. 2 is an enlarged view illustrating a moving part of the capsule type micro-robot moving system in FIG. 1;

FIGS. 3 and 4 are side sectional views illustrating a movement mechanism of the capsule type micro-robot moving system in FIG. 1;

FIG. 5 is a sectional view taken along the line V-V of an assembly of the capsule type micro-robot moving system in FIG. 1;

DETAILED DESCRIPTION OF PREFERRED EMBODIMENTS

Hereinafter, a capsule type micro-robot moving system according to a preferred embodiment of the present invention will be described.

Figure 1:
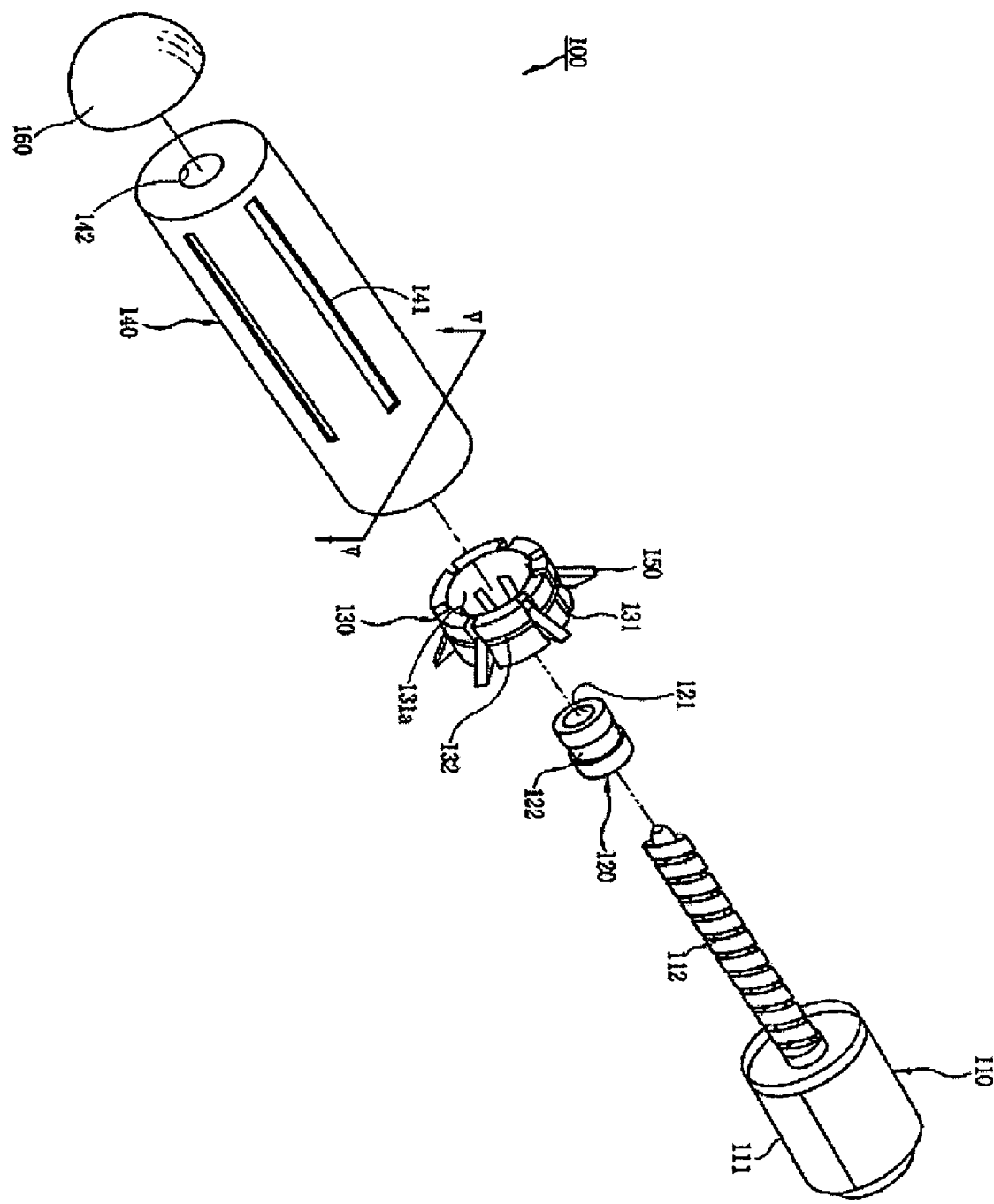
Figure 2:
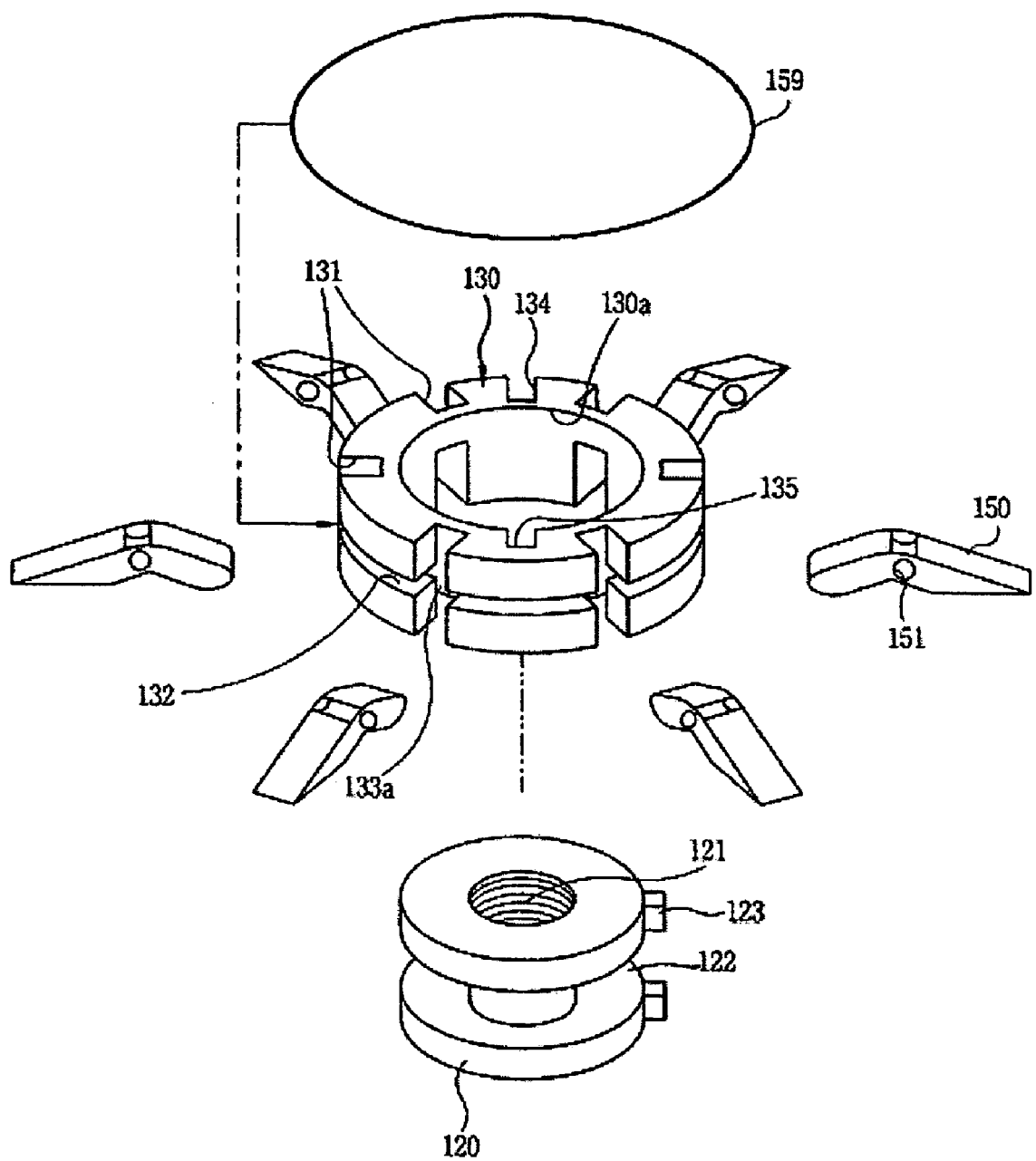

As shown in FIGS. 1 and 6, the capsule type micro-robot moving system 100 according to the first preferred embodiment of the present invention includes a driving part 110 for moving a capsule, an inner cylinder 120 moving in the longitudinal direction of the capsule by the driving part 110, an outer cylinder 130 having a hollow part 130a to surround the inner cylinder 120, the capsule 140 for enclosing the inner cylinder 120 and the outer cylinder 130, limbs 150 rotatably fixed to the outer cylinder 130 to be folded inward the capsule 140 or unfolded outward the capsule 140 according to the movement direction, and a semi-spherical camera 160 provided in a head of the capsule 140.

The driving part 110 includes a subminiature motor 111 installed in a tail of the capsule 140 and a screw rod 112 rotated in association with a rotation shaft of the subminiature motor 111. The subminiature motor 111 is driven by a battery.

Figure 3:
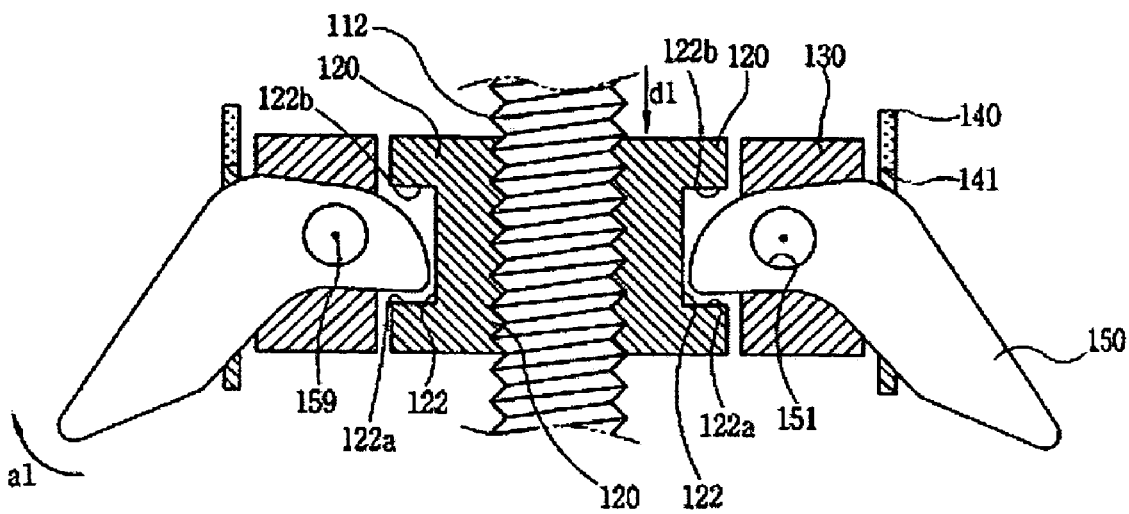
Figure 4:
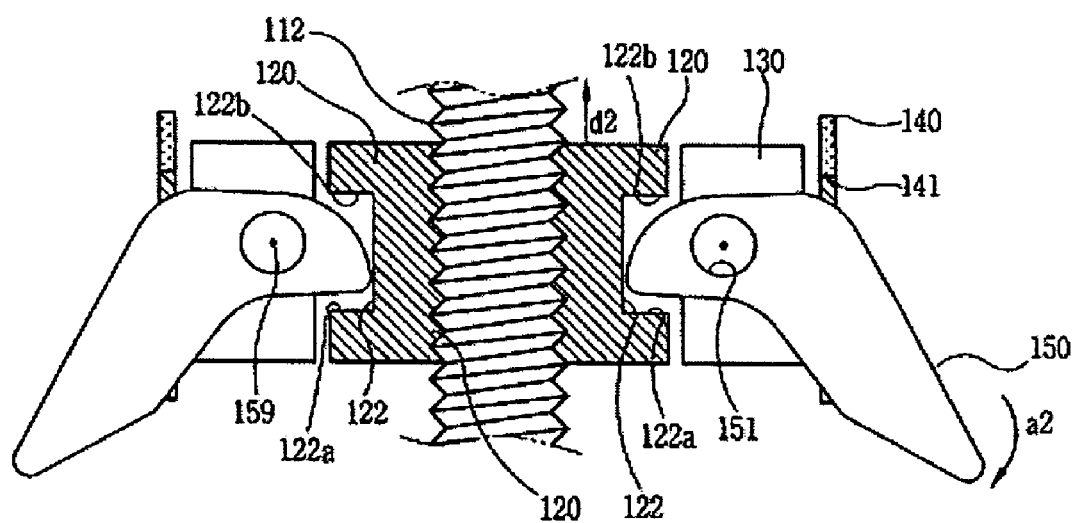

The inner cylinder 120 has a thread 121 formed in a central penetrated portion fastened with the screw rod 112 of the driving part 110 and a locking groove 122 formed in the mid portion of the outer circumference thereof in the circumferential direction. The locking groove 122 provides a space for accommodating parts of the limbs 150, as shown in FIGS. 3 and 4, according to the movement of the inner cylinder 120, due to the interference with the limbs 150, the limbs 150 rotate about a wire 159 to fold or unfold. Moreover, as shown in FIGS. 3 and 4, the locking groove 122 is caved to form vertical walls 122a and 122b such that its bottom is flat.

The outer cylinder 130 has grooves 131 formed in the outer circumference of the outer cylinder 130 in the rotational direction of the limbs 150 (in the longitudinal direction of the outer cylinder) such that the limbs 150 can be rotated by a predetermined angle, and hinge recess 132 formed in the outer circumference in the circumferential direction in series such that a wire 159 penetrating hinge holes 151 is placed. First exposing holes 133a penetrating the insides of the grooves 131 are formed such that parts of the limbs 150 are accommodated in the locking groove 122 of the inner cylinder 120.

The capsule 140 serves as a body of a robot, and has the outer surface coated with an anti-adhesion coating agent for reducing friction against organs during the movement such that the capsule 140 can rapidly move in organs, and second exposing holes 141 are formed long in the outer circumference of the capsule 140 in the longitudinal direction such that the capsule 140 can move after the limbs 150 directly contact and stick to the wall of the organ. A head of the capsule 140 is formed with an opening 142 for installing the camera 160.

Here, the second exposing holes 141 are aligned with the limbs 150, and since, as shown in FIG. 1, six limbs are installed in the outer cylinder 130, the number of the second exposing holes 141 is six.

The six limbs 150 are formed in the circumference of the outer cylinder 130 every 60 degrees to stick to the wall of the organ with more contact points. By doing so, friction between the organ 10 and the limbs 150 can be effectively guaranteed. Preferably, in the ends of the limbs 150 contacting the wall of the organ 10, in order to obtain large friction, a plurality of minute protrusions 153 is formed.

Figure 5:
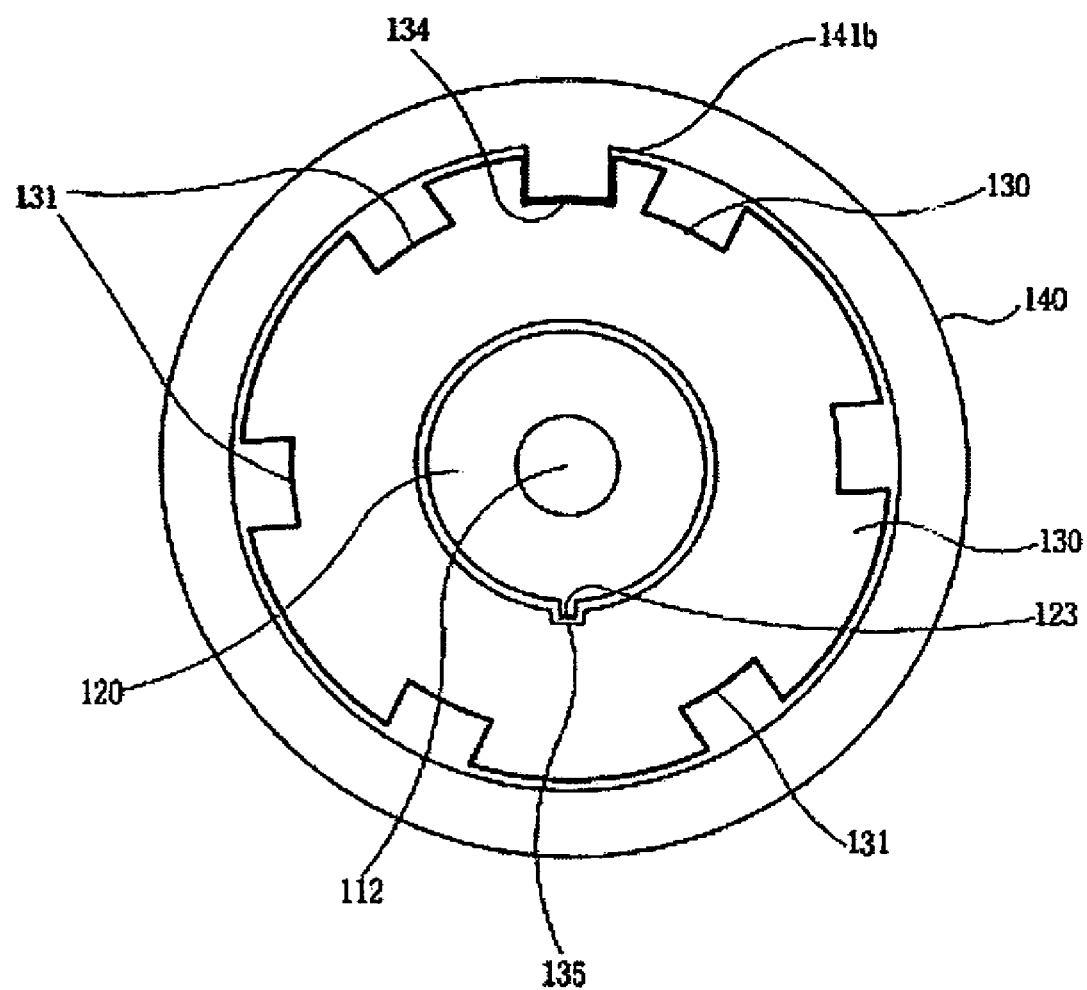

Here, that the limbs 150 are fixed to the outer cylinder 130 to rotate is implemented by which a single wire 159 penetrates the hinge holes 151 of the limbs 150, the parts of the limbs 150 are inserted into the first exposing holes 133a, and the wire 159 is placed on the hinge recess 132. As shown in FIGS. 3 and 5, the parts of the limbs 150 inserted into the first exposing holes 133a are accommodated in the locking groove 122 of the inner cylinder 120 installed in the mid portion of the outer cylinder 130. By doing so, the limbs 150 are installed in the grooves 131 of the outer cylinder 130 to rotate. When the inner cylinder 120 moves against in the longitudinal direction of the capsule 140, the inserted parts of the limbs 150 interferes with the locking groove 122 of the inner cylinder 120 so that the limbs 150 are folded or unfolded according to the movement direction of the inner cylinder 120.

In the first preferred embodiment of the present invention as described above, when the screw rod 112 is rotated by the motor 111, the inner cylinder 120 must be moved in the longitudinal direction of the capsule 140. To this end, since the rotation of the inner cylinder 120 must be restricted, as shown in FIG. 5, a rotation prevention protrusion 123 is formed in the outer circumference of the inner cylinder 120 and a rotation prevention recess 135 is formed over whole inner circumference of the outer cylinder 130 in the longitudinal direction to be engaged with the rotation prevention protrusion 123. Thus, the inner cylinder 120 linearly moves against the outer cylinder 130 in the longitudinal direction, but its rotation is restricted.

Similarly, the rotation of the outer cylinder 130 is restricted within the capsule 140. This is designed for the purpose of preventing the outer cylinder 130 and the inner cylinder 120 from rotating together and of arranging the limbs 150 installed to the outer cylinder 130 between the second exposing holes 141 of the capsule 140. To this end, the capsule 140 has protrusions 141b formed in the inner circumference of the capsule 140, and the outer cylinder 130 has grooves 134 formed over the longitude of the outer circumference of the outer cylinder 130 to be engaged with the protrusions 141b.

The capsule type micro-robot moving system according to the first preferred embodiment of the present invention is assembled as follows.

Firstly, the motor 11 is coupled with the screw rod 112 to form the driving part 110. Next, the screw rod 112 is coupled with the inner cylinder 120 by screws, and the inner cylinder 120 is surrounded by the outer cylinder 130. In this state, after the wire 159 penetrates the hinge holes 151 of the six limbs 150 to connect them with each other, respective limbs 150 are inserted into the locations of the first exposing holes 133a penetrating the outer circumference of the outer cylinder 130 and the free ends of the wire 159 is bound and the wire 159 is inserted into the hinge recess 132 and is placed therein. At that time, since the parts of the limbs 150 penetrate the outer cylinder 130 and are accommodated in the space of the locking groove 122 of the inner cylinder 120, after fixing the limbs 150 to the outer cylinder 130, the inner cylinder 120 is not separated from the outer cylinder 130.

After that, in order to engage the grooves 134 of the outer cylinder 130 with the protrusions 141b of the inner circumference of the capsule 140, an assembly of the inner cylinder 120, the outer cylinder 130, and the driving part 110 is inserted into and fixed to the capsule 140. In the state of inserting the assembly into the capsule 140, since the first exposing holes 133a of the outer cylinder 130 are aligned with the second exposing holes 141 of the capsule 140, the unfolded limbs 150 penetrate the exposing holes 133a and 141 and expose over the capsule 140.

Next, the camera 160 is fixed to the head of the capsule 140 the capsule type micro-robot moving system 100 according to the first preferred predetermined direction, since the limbs 150 are exposed over the wall of the organ 10 and hold the wall of the organ 10, the limbs 150 and the outer cylinder 130 keep in stopping on the wall of the organ and the inner cylinder 120 comes close to the driving part 110. In other words, the state depicted in FIG. 6B is changed into the state depicted in FIG. 6D, and the capsule is relatively advanced.

Figure 6A:
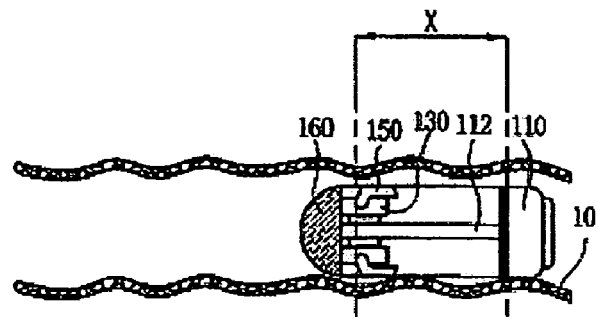
FIGS. 6A to 6G are schematic views illustrating the movement of the capsule type micro-robot moving system in FIG. 1.
Figure 6B:
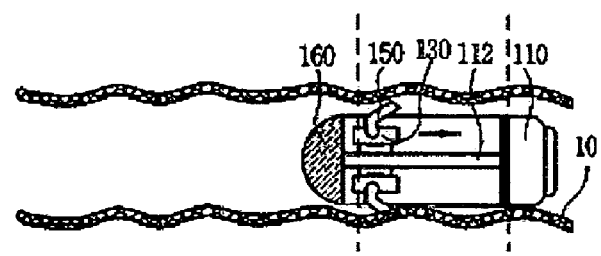
Figure 6C:
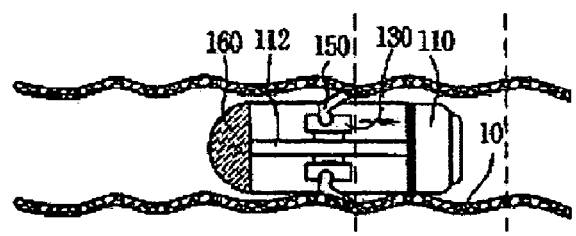
Figure 6D:
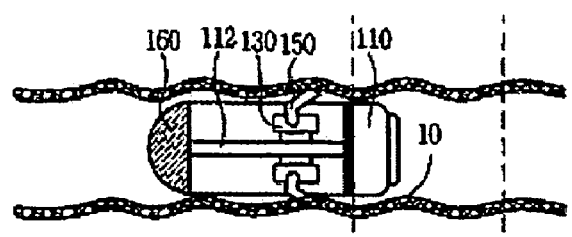
Figure 6E:
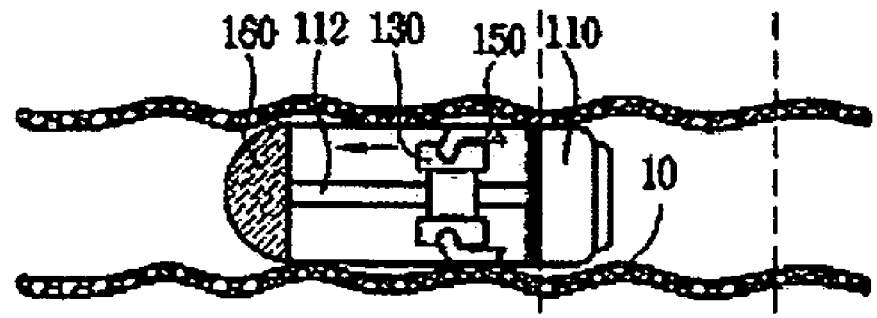
Figure 6F:
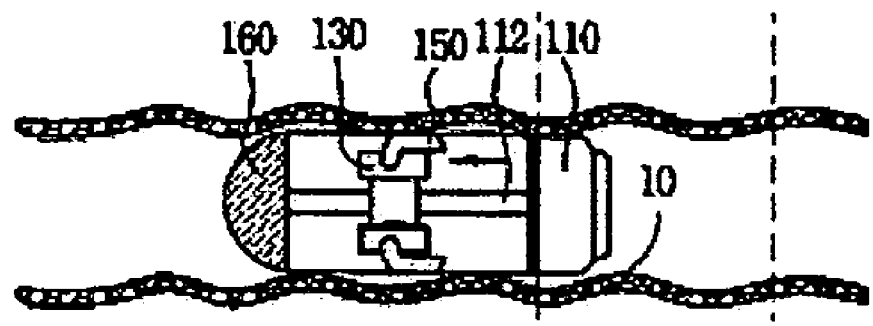
Figure 6G:
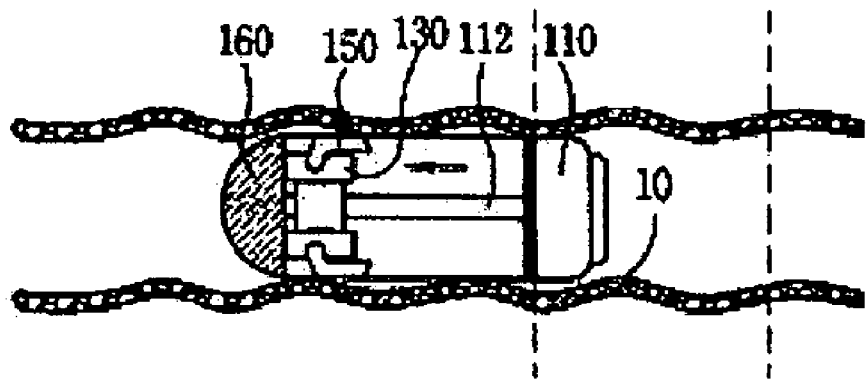

In the state referring to FIG. 6D that the capsule moves as maximum as possible, when the screw rod 112 rotates in the opposite direction, according to the principle in FIG. 4, the inner cylinder 120 goes up in the upper direction d2 and the limbs 150 rotate (a2) inward the capsule 140 and are folded inward the capsule 140. When the screw rod 112 further rotates in the opposite direction, since the limbs 150 does not contact the wall of the organ 10, the capsule 140 keeps in stopping on the wall of the organ 10 and the distance between the driving part 110 and the inner cylinder 120 is farther and the state depicted in FIG. 6G is established. In other words, the state in FIG. 6G is identical to the state in FIG. 6A, but the capsule 140 advances by the distance indicated by the numeral x in FIG. 6A.

The process in FIGS. 6A to 6G are repeated so that the capsule type micro-robot according to the first preferred embodiment of the present invention moves forward.

Meanwhile, although in the first preferred embodiment the driving part includes the subminiature motor 111 and the screw rod 112 rotate in association with the motor 111, various linear drivers using such as a PZT linear ultrasonic motor may be utilized. Although in order to restrict the relative rotational displacement between the inner cylinder 120 and the outer cylinder 130, the recesses 135 and the protrusions 123 engaged with each other are formed, even when instead a fixed guide rod (not shown) is formed to traverse the longitude of the inner cylinder 120, the same effect can be achieved.

In addition to the capsule type micro-robot moving system according to the first preferred embodiment of the present invention moving forward only, in another preferred embodiment of the present invention, it is provided a capsule type micro-robot moving system capable moving forward and backward.

In the description of another preferred embodiment of the present invention, for the clear description the same numerals are assigned to the identical or similar components of the first preferred embodiment of the present invention, and the description thereof will be omitted.

Figure 7:
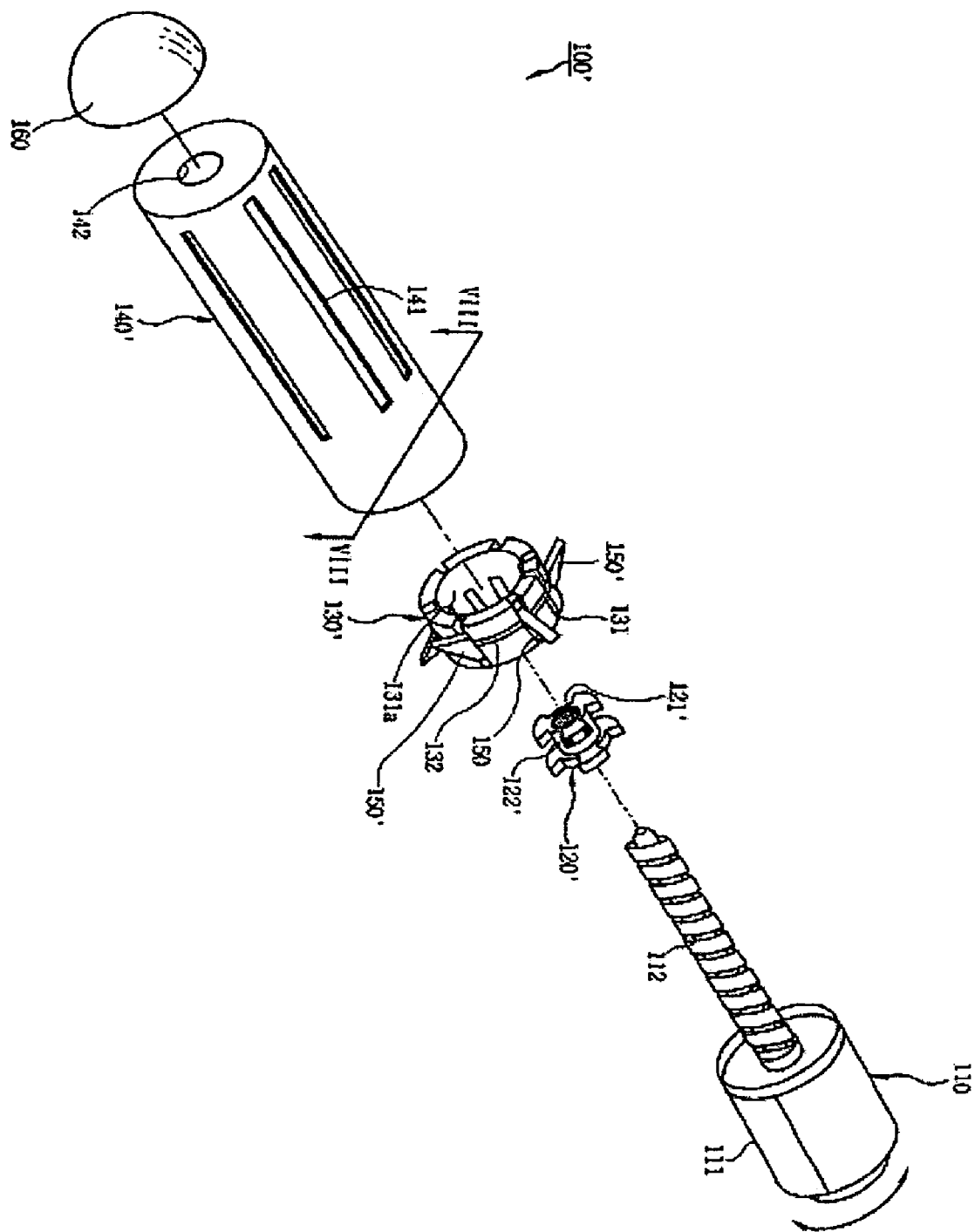
FIG. 7 is an exploded perspective view illustrating a capsule type micro-robot moving system according to another preferred embodiment of the present invention.

As show in FIG. 7, the capsule type micro-robot moving system 100' according to another preferred embodiment of the present invention includes a driving part 110 for moving the capsule, an inner cylinder 120' moving in the longitudinal direction of the capsule, an outer cylinder 130' formed with a hollow part 130a to surround the inner cylinder 120', the capsule 140 for enclosing the inner cylinder 120' and the outer cylinder 130', limbs 150 and 150' rotatably fixed to the outer cylinder 130' to be folded inward the capsule 140 or unfolded outward the capsule 140 according to the movement direction, and a semi-spherical camera 160 provided in a head of the capsule 140.

The inner cylinder 120' has a thread 121' formed in a central embodiment of the present invention is completely assembled.

Hereinafter, the operation principle of the capsule type micro-robot moving system according to the first preferred embodiment of the present invention will be described.

When the screw rod 112 of the driving part 110 is rotated in a predetermined direction, as shown in FIG. 3, the inner cylinder 120 runs down in the lower direction d1, an upper wall 122b of the locking groove 122 of the inner cylinder 120 presses the limbs 150 down so that the limbs 150 are unfolded in the direction indicated as a1 in the drawing.

When the screw rod 112 of the driving part 110 is rotated in the opposite direction, as shown in FIG. 4, the inner cylinder 120 runs up in the upper direction d2, a lower wall 122a of the locking groove 122 of the inner cylinder 120 presses the limbs 150 up so that the limbs 150 are unfolded in the direction indicated as a2 in the drawing.

Hereinafter, according to the above principle, it will be described the principle that the capsule type micro-robot moving system 100 according to the first preferred embodiment of the present invention moves on the wall of the organ 10.

FIG. 6A shows the unfolded limbs 150. In the state as shown in FIG. 6A, when the screw rod 112 is rotate in the predetermined direction, according to the principle illustrated in FIG. 3, the inner cylinder 120 goes down in the lower direction d1 and the limbs 150 rotate (a1) out of the capsule 140 and are unfolded (See FIG. 6B). When the screw rod 112 further rotates in the penetrated portion fastened with a screw rod 112 of the driving part 110 and a locking groove 122' formed in the mid portion of the outer circumference thereof in the circumferential direction. Lateral protrusions 126' of the sides of the locking groove 122' are formed with locking protrusions 125' protruded in the radial direction every 120 degrees and there is no protrusion therebetween 126'. Due to this configuration, one of groups of the alternately installed limbs 150 and 150' interferences with the locking protrusions 125' when the inner cylinder 120' moves and the other does not interfere therewith regardless of the movement of the inner cylinder 120'.

The outer cylinder 130' has first exposing holes 133a penetrating the insides of the grooves 131 and formed in the circumferential direction at regular intervals such that parts of the limbs 150 are accommodated in the locking groove 122 of the inner cylinder 120'.

Figure 8:
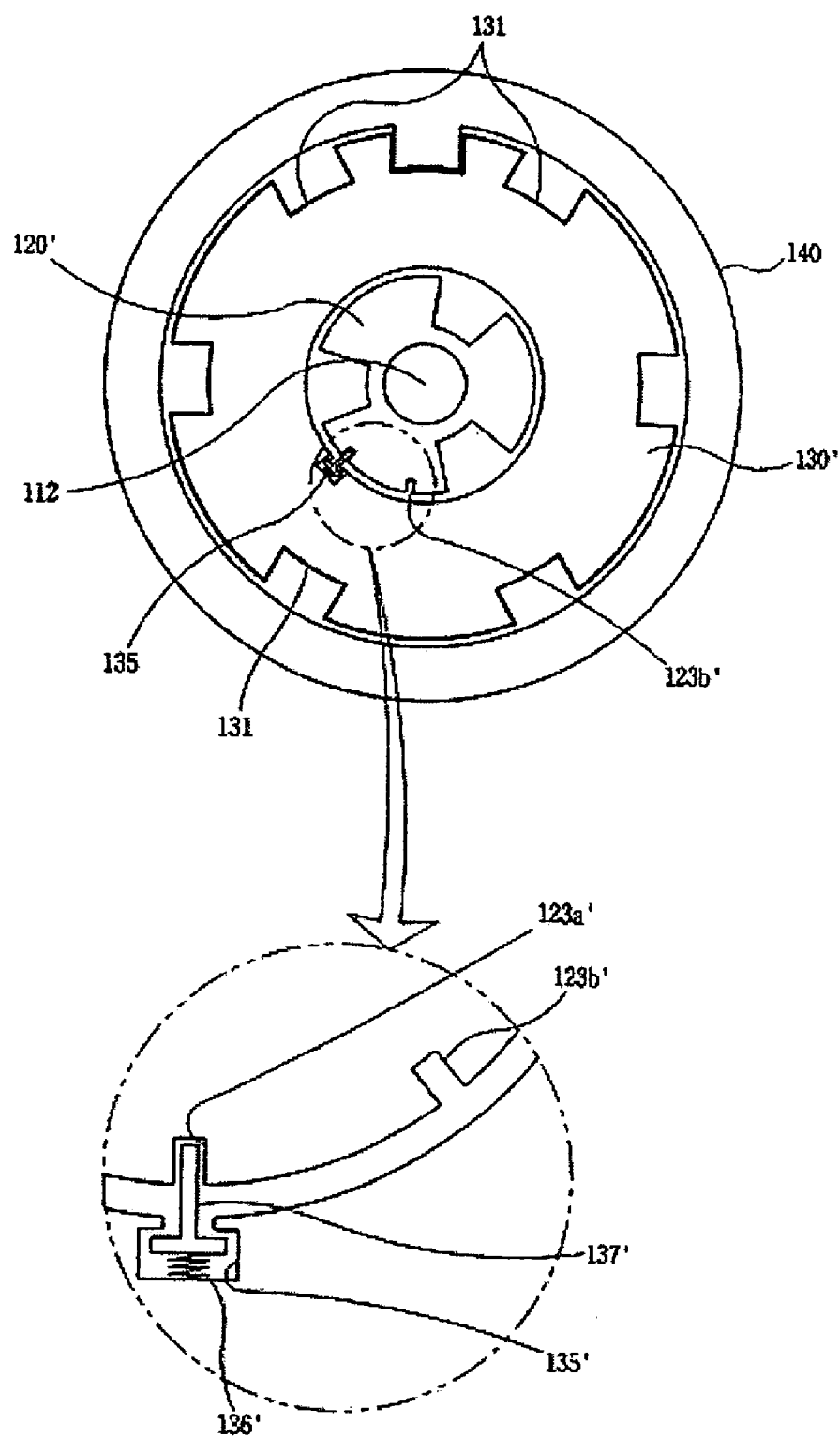
FIG. 8 is a sectional view taken along the line VIII-VIII in FIG. 7.

Here, in order to interfere one of the groups of the alternately installed limbs 150 and 150' with each other, a structure illustrated in an enlarged view of FIG. 8 is added. In other words, in any outer circumference of the locking protrusions 125' of the inner cylinder 120', recesses 123a' and 123b' are formed at 60 degrees corresponding to the distance between the limbs 150 and 150', and in a recess 135' formed in the inner circumference of the outer cylinder 130', a T-shaped pin 137' inserted into one of the recesses 123a' and 123b' and an actuator 136' made of a shape memory alloy (SMA) to actuate the pin 137' are installed. Since the SMA actuator 136' is applied by an electric current, when the electric current is applied thereto, the actuator 136' is contracted such that the end of the pin 137' comes out of the recess 123a', and at that time, the motor of the driving part 110 is rotated so that the relative rotation between the inner cylinder 120' and the outer cylinder 130' can be achieved. After that, when the outer cylinder 130' rotates by 60 degrees with respect to the inner cylinder 120', the end of the pin 137' fixed to the outer cylinder 130' is inserted into the recess 123b' so that the relative movement between the inner cylinder 120' and the outer cylinder 130' is restricted.

The capsule 140 serves as a body of a robot, and has the outer surface coated with an anti-adhesion coating agent for reducing friction against organs during the movement such that the capsule 140 can rapidly move in organs, and second exposing holes 141 are formed long in the outer circumference of the capsule 140 in the longitudinal direction such that the capsule 140 can move after the limbs 150 and 150' directly contact and stick to the wall of the organ.

Figure 9:
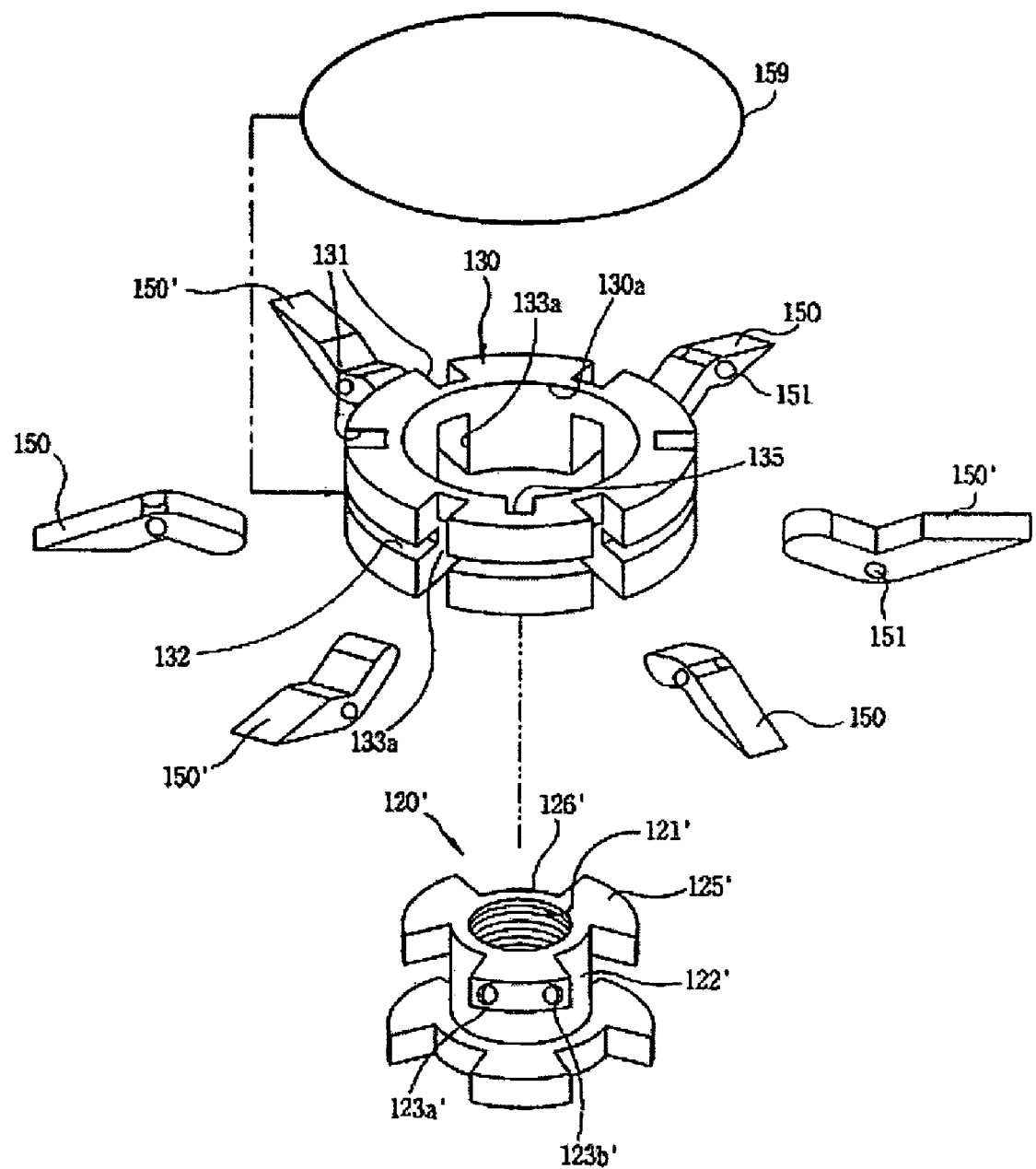
FIG. 9 is an enlarged exploded perspective view illustrating a movement part of the capsule type micro-robot moving system in FIG. 7.

The six limbs 150, as shown in FIG. 9, are installed alternately in the direction in the outer circumference of the outer cylinder 130' one by one at 60 degrees.

Figure 14A:
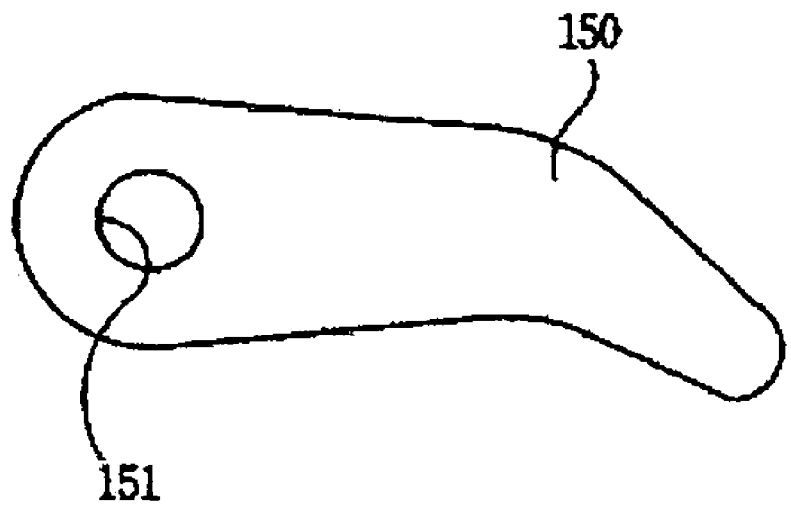
FIGS. 14A to 14C are schematic views illustrating the shape of limbs in FIG. 12.
Figure 14B:
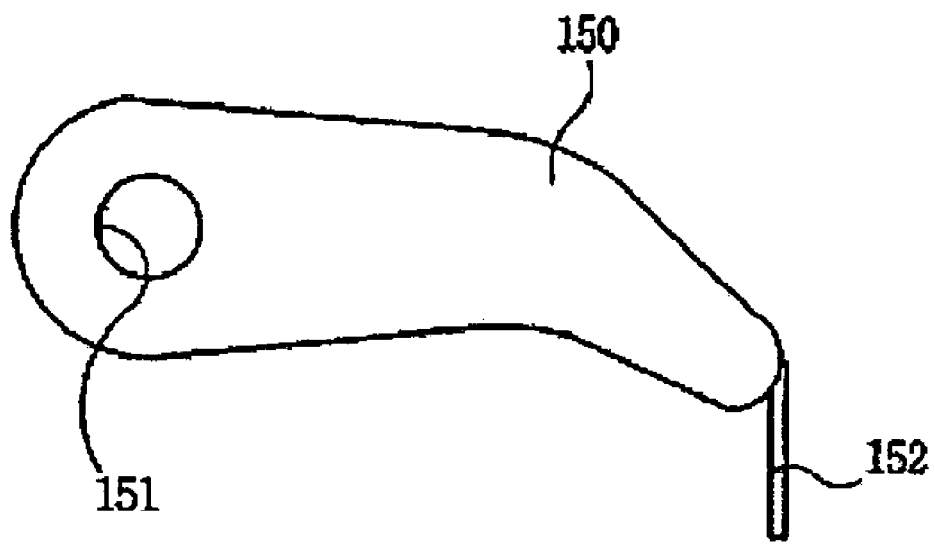
Figure 14C:
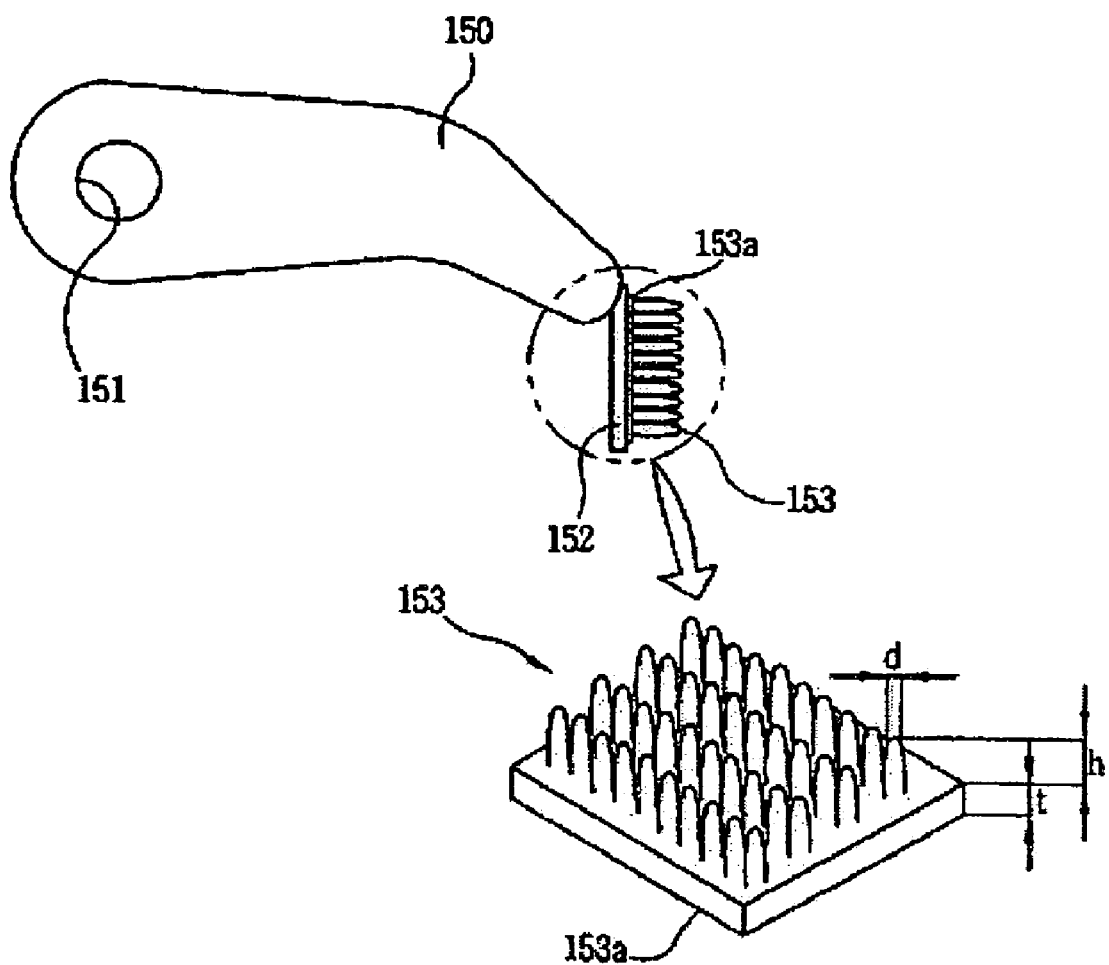

Meanwhile, as shown in FIG. 14A, it is preferred that the ends of the limbs 150 are rounded to prevent the wall of the organ from damaging. However, in order to maintain a driving force for the forward motion and the backward motion, the limbs 150 are preferably made of rigid bodies. Meanwhile, as shown in FIG. 14B, in order to grip the wall of the organ more firmly, it is more preferred that the ends of the limbs 150 are installed with elastic bodies or flexible joints 152 smoothly bent against the limbs 150. Further, as shown in FIG. 14C, to the ends or the flexible joints 152, contacting the wall of the organ, of the limbs 150, adhesive plates 153 with a high adhesive power may be attached. Here, the adhesive plates 153 have a structure similar as cilia in the sole of a foot of a lizard, and, for example, each of the cilia has a diameter d about hundreds nm to few μm and a height h about few μm to tens μm, is formed in micro-patterns or nano-patterns, and bottoms 153a of the adhesive plates 153 may be made of flexible materials to have a thickness about 0.5 mm. In other words, a ratio of the diameter d to the height h of the cilia can be applied within the range of about 1:1 to 1:100 according to the use. The structure of the adhesive plates 153 is disclosed in U.S. Pat. No. 6,737,160B1, entitled "Adhesive microstructure and method of forming same".

Figure 10:
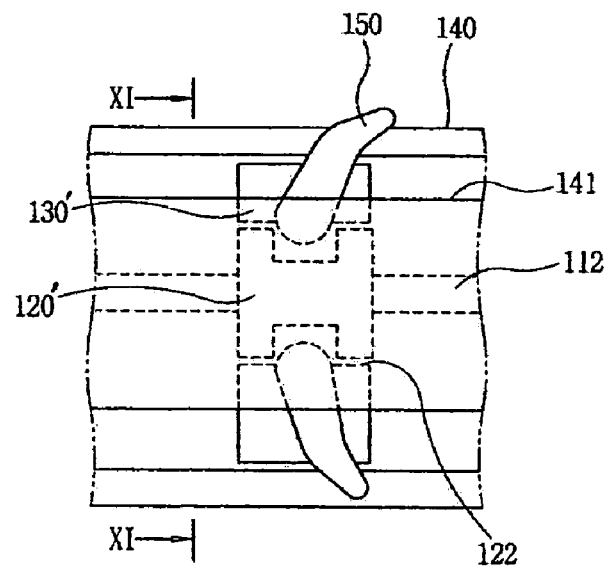
FIG. 10 is a side view illustrating the capsule type micro-robot moving system moves forward.
Figure 11:
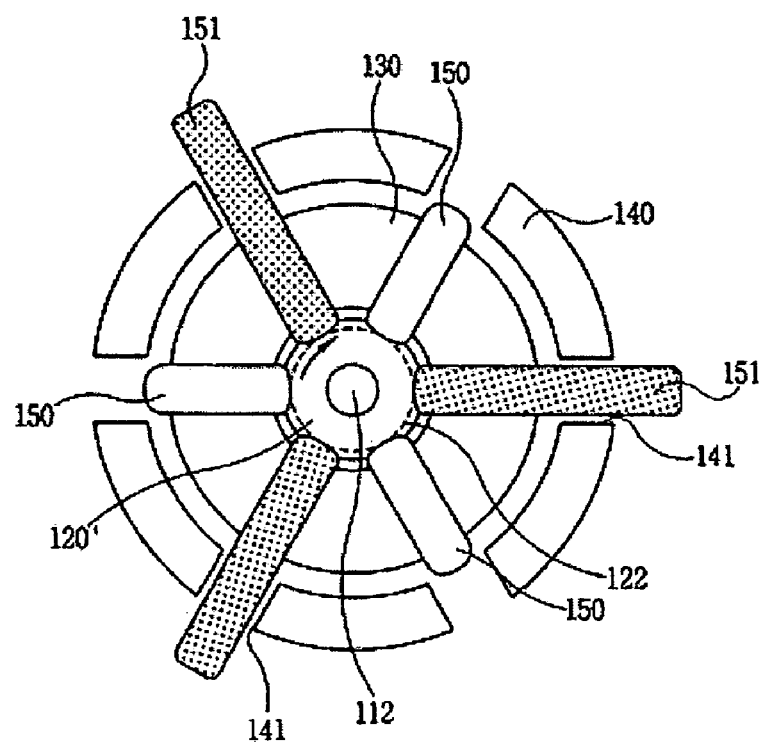
FIG. 11 is a sectional view taken along the ling XI-XI in FIG. 10.
Figure 12:
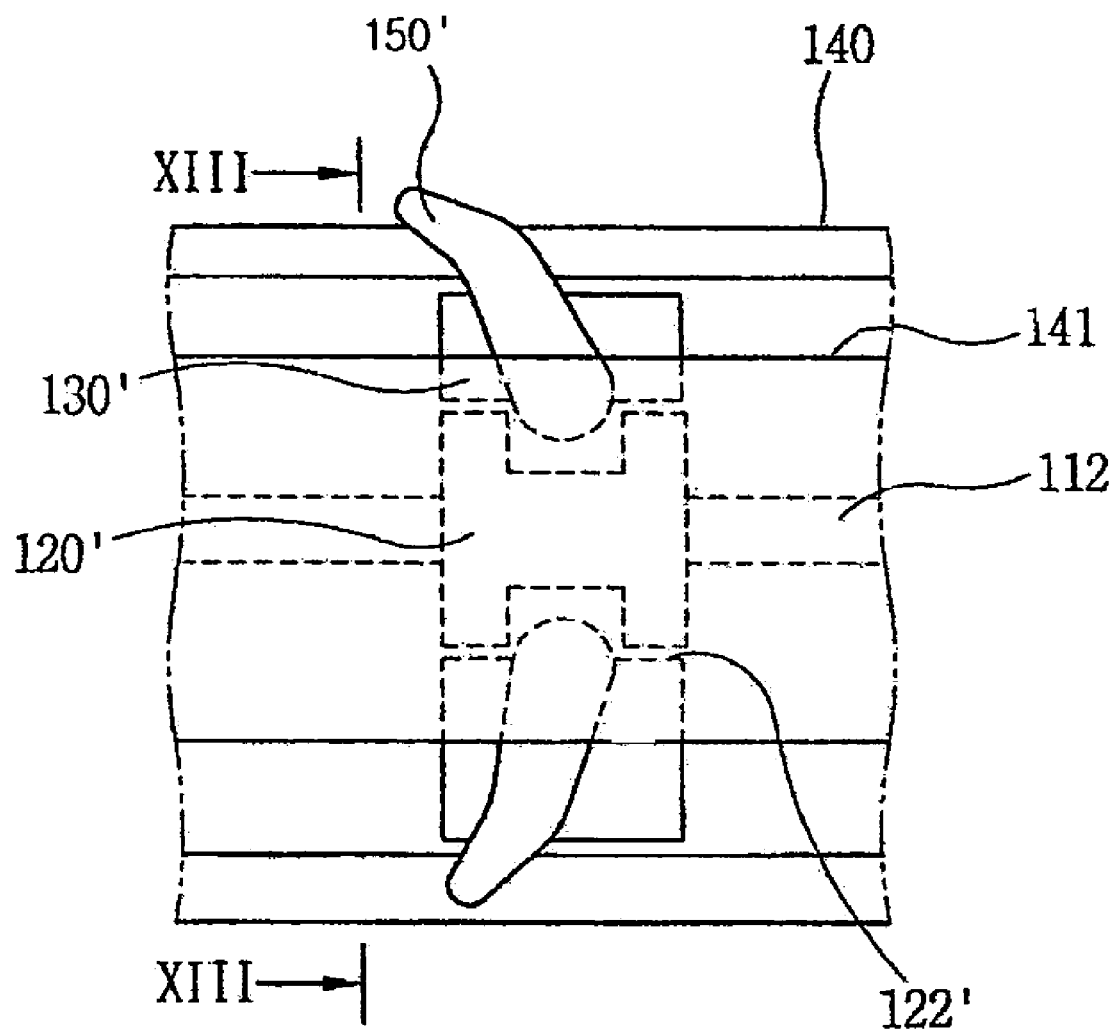
FIG. 12 is a side view illustrating the capsule type micro-robot moving system moves backward.
Figure 13:
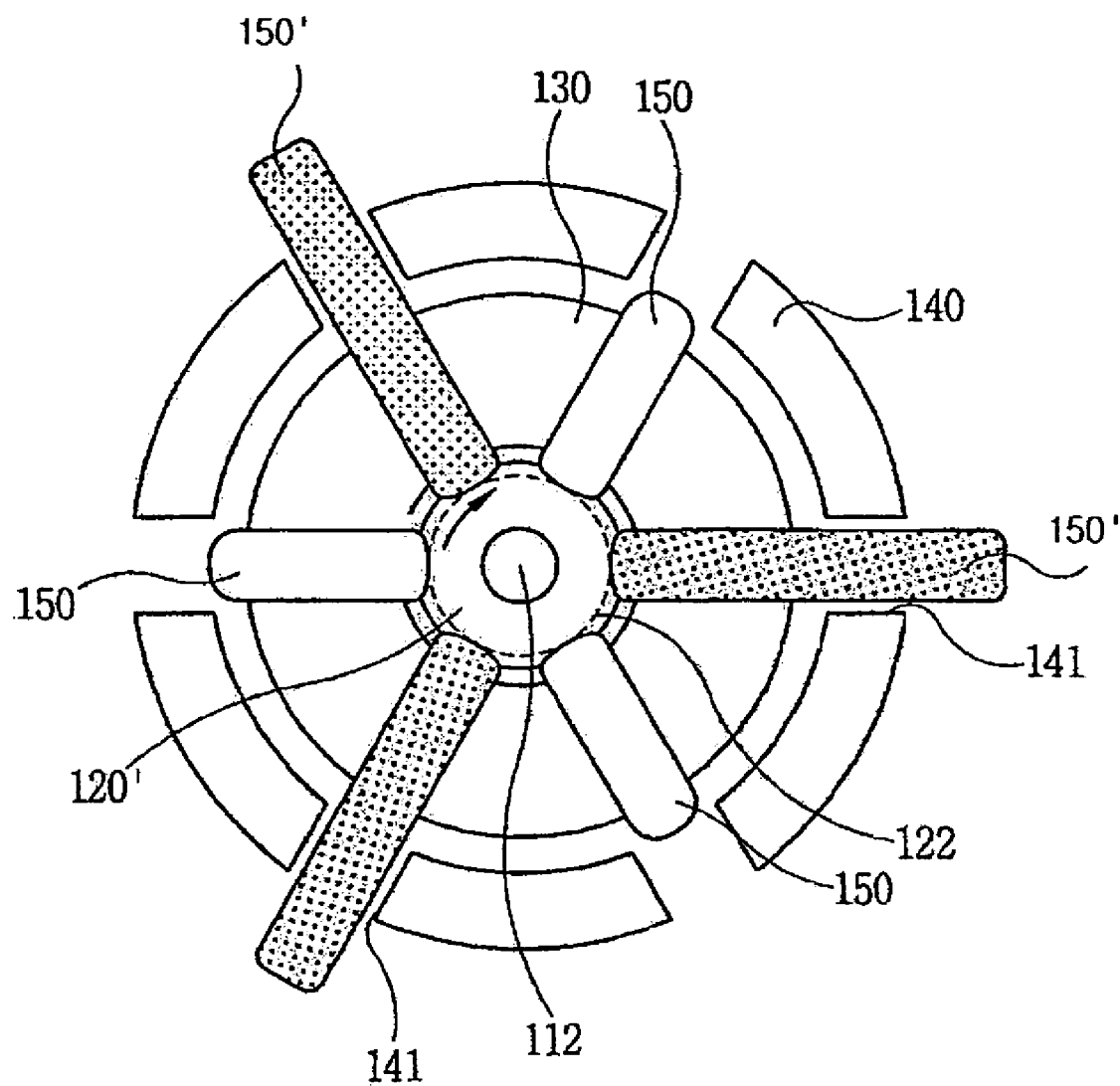
FIG. 13 is a sectional view taken along the line XIII-XIII in FIG. 12.

The preferred embodiment 100' of the present invention structured as described above is similar as the first preferred embodiment 100 in view of the operating principle. In more detail, as shown in FIGS. 10 and 11, in the state that only the group of the limbs 150 bent backward interferes with the locking protrusions, 125' of the inner cylinder 120', when the inner cylinder 120' moves, the forwardly-bent limbs 150' cannot be unfolded out of the capsule 140 despite of the movement of the inner cylinder 120', however since the group of the backwardly-bent limbs 150 repeats the folding and unfolding through the second exposing holes 141 of the capsule 140 and advances because of interference with the protrusions 125' of the inner cylinder 120'.

To move the capsule type micro-robot moving system 100' backward according to the using purpose and/or need, when a predetermined current is applied to the actuator 136' of the outer cylinder 130', the actuator 136' made of the SMA is so contracted that the pin 137' fixed to the end of the actuator 136 comes out of the recess 123a formed in the inner cylinder 120'. After that, when the motor of the driving part 110 is rotated, since the association between the inner cylinder 120' and the outer cylinder 130' is released, only the inner cylinder 120' is relatively rotated with respect to the outer cylinder 130. When the motor of the driving part 110 is controlled to rotate by about 60 degrees and at the same time the current applied to the actuator 136' is interrupted, the pin 137' is inserted into other recess 123b' spaced apart therefrom by 60 degrees, only the backward-oriented limbs 150' interfere with the locking protrusions 125' of the inner cylinder 120', and the forward-oriented limbs 150 do not interfere with the locking protrusions 125' further. In other words, an association in which the inner cylinder 120' and the outer cylinder 130' rotate together is established. In this state, when the driving part 110 is driven to move the inner cylinder 120', like the principle of the first preferred embodiment, the backward movement can be achieved. Thus, the capsule can be moved forward and backward repeatedly as one wants.

Meanwhile, although the limbs 150 and 150' are respectively six in this preferred embodiment 100', if necessary, the more large number of the limbs 150 and 150' may be utilized to hold and move on the wall of the organ.

Although a few embodiments of the present invention have been shown and described, it would be appreciated by those skilled in the art that changes might be made in this embodiment without departing from the principles and spirit of the invention, the scope of which is defined in the claims and their equivalents.

As described above, the present invention provides a capsule type micro-robot moving system, which is structured such that a head is formed in a semi-spherical shape and the outer surface of the capsule is coated with an anti-adhesion coating agent for reducing friction against organs during the movement, particularly, is structured to move as long as a linear stroke corresponding to the distance between the driving part and the inner cylinder in the state that the limbs folded in and unfolded out of the capsule completely contact and stick to the walls of the organs, resulting in providing the reliability and moving more rapidly.

Moreover, the capsule type micro-robot moving system of the present invention can perform the necessary tasks such as the sampling, the image capturing, the monitoring, or the like in the state that the limbs completely contact the walls of the organs.

In addition, the capsule type micro-robot moving system of the present invention can be utilized as a capsule type endoscope and a moving device capable of moving in a circular pipe or other rough circumstances.

Further, since the capsule type micro-robot moving system of the present invention can move forward and backward, the capsule type micro-robot moving system used as a capsule type endoscope can be moved back to the spot where passed over and required to inspect again so that the system can satisfy the vast purpose of using the system.

Since the protrusions of the ends of the limbs are formed in the forms of minute cilia, damage of the wall of the organ that would be occurred during the movement in holding the wall of the organ can be remarkably reduced and the system can be moved more smoothly.

As described above, since the capsule type micro-robot moving system has a simple and effective structure, when the system is applied to a capsule type endoscope for the inspection and diagnosis of human small and large intestines, the system of the present invention allows the endoscope inspection more rapid and convenient than the conventional endoscope without a moving function moved due to the intestine activities, and can be utilized in a surgical operation of human digestive organ. In addition, the capsule type micro-robot moving system of the present invention is easily fabricated with low manufacturing costs and is very small in size such as a diameter is under 11 mm and the length is under 26 mm, the patient's pain during the endoscope inspection can be minimized.

What is claimed is:

1. A capsule type micro-robot moving system comprising:
   at least one limb folded when moving forward and unfolded to contact a wall of an organ when moving backward,
   an inner cylinder having a locking groove formed in the outer circumference thereof;
   a driving part for moving the inner cylinder in the longitudinal direction;
   an outer cylinder having a hollow part formed therein to surround the inner cylinder;
   at least one first exposing hole penetrating the outer circumference of the outer cylinder in the longitudinal direction;
   the limb hinged to the outer cylinder to rotate by a predetermined range, exposed over the first exposing hole when the limb is unfolded due to the rotation, and hided in the first exposing hole when the limb is folded due to the rotation;
   a capsule for surrounding the outer cylinder; and
   at least one second exposing hole aligned with the first exposing hole respectively and formed in the longitudinal direction of the capsule such that the limb is exposed over the capsule when the limb is unfolded;
   wherein the limb is folded or unfolded by the interferences between the locking groove and the limb according to the movement direction of the inner cylinder.

2. The capsule type micro-robot moving system as claimed in claim 1, wherein the limb is formed as having a bended portion.

3. The capsule type micro-robot moving system as claimed in claim 1, wherein the capsule type micro-robot has a plurality of limbs.

4. The capsule type micro-robot moving system as claimed in claim 3, wherein the outer cylinder has a continuous hinge recess formed in the circumferential direction thereof, and wherein a rotation center hole is formed at the rotation center of the respective limb, and that a wire passes through the rotation center holes of the limbs in series and is placed in the hinge recess.

5. The capsule type micro-robot moving system as claimed in claim 4, wherein the limb is formed as having a bent portion, and all the limbs having a bent portion are installed to face one direction.

6. The capsule type micro-robot moving system as claimed in claim 3, wherein the limbs comprise:
   a first group of the limbs having a bent portion hinged to the outer cylinder to rotate by a predetermined range so as to face one direction; and
   a second group of the limbs having a bent portion hinged to the outer cylinder to rotate by a predetermined range so as to face the opposite direction to the first group thereof.

7. The capsule type micro-robot moving system as claimed in claim 6, wherein the limbs in the first group and the limbs in the second group are arranged alternately.

8. The capsule type micro-robot moving system as claimed in claim 7, wherein the outer cylinder is able to rotate by a predetermined amount with respect to the inner cylinder,
   the inner cylinder has locking protrusions formed at the sides of the locking groove such that when the inner cylinder is rotated by a predetermined angle, the first group interferes with the locking protrusions and the second group is free between the locking protrusions so that only the first group is folded and unfolded according to the movement of the inner cylinder, and
   when the inner cylinder is rotated reversely by the predetermined angle, the second group interferes with the locking protrusions and the first group is free between the locking protrusions so that only the second group is folded and unfolded according to the movement of the inner cylinder.

9. The capsule type micro-robot moving system as claimed in claim 1, further comprising:
   at least one rotation prevention recess formed in the outer circumference of the outer cylinder; and
   at least one rotation prevention protrusion formed in the inner circumference of the capsule to be engaged with the rotation prevention recess.

10. The capsule type micro-robot moving system as claimed in claim 1, wherein the inner cylinder has a hollow part penetrating the central portion thereof, the inner cylinder has at least one groove formed in the outer circumference of the inner cylinder in the longitudinal direction to prevent the inner cylinder from rotating within the outer cylinder;

the outer cylinder has a protrusion formed in the inner circumference of the outer cylinder and engaged with the groove; and the driving part comprises:

a motor installed to the rear side of the capsule; and a screw rod rotated in association with the rotation of the motor and fastened in the hollow part of the inner cylinder.

11. The capsule type micro-robot moving system as claimed in claim 1, wherein the inner cylinder has a hollow part penetrating the central portion thereof, the inner cylinder has a protrusion formed in the outer circumference of the inner cylinder to prevent the inner cylinder from rotating within the outer cylinder;

the outer cylinder has a groove formed in the inner circumference of the outer cylinder in the longitudinal direction and engaged with the protrusion;

the driving part comprises:

a motor installed to the rear side of the capsule; and a screw rod rotated in association with the rotation of the motor and fastened in the hollow part of the inner cylinder.

12. The capsule type micro-robot moving system as claimed in claim 1, further comprising:

a guide hole penetrating the inner cylinder in the longitudinal direction; and a guide rod penetrating and fixed in the guide hole;

wherein the driving part comprises:

a motor installed to the rear side of the capsule; and a screw rod rotated in association with the rotation of the motor and fastened in the hollow part of the inner cylinder.

13. The capsule type micro-robot moving system as claimed in claim 1, further comprising a camera installed in a head of the capsule.

14. The capsule type micro-robot moving system as claimed in claim 13, wherein the camera has a semi-spherical shape.

15. The capsule type micro-robot moving system as claimed in claim 1, wherein a plurality of minute protrusions is formed in the ends of the unfolded limbs.

16. The capsule type micro-robot moving system as claimed in claim 15, wherein the minute protrusions comprise cilia.

17. The capsule type micro-robot moving system as claimed in claim 16, wherein flexible joints are formed in the ends of the limbs.

18. The capsule type micro-robot moving system as claimed in claim 1, wherein the capsule is coated with an anti-adhesion agent.

19. The capsule type micro-robot moving system as claimed in claim 1, wherein the driving part comprises a PZT linear motor.

20. The capsule type micro-robot moving system as claimed in claim 1, further comprising a communication unit for communicating the inside of the capsule with the exterior of the capsule.

21. The capsule type micro-robot moving system as claimed in claim 1, wherein the locking groove is vertically caved to form a flat bottom.

22. The capsule type micro-robot moving system as claimed in claim 1, wherein adhesive plates are made of high frictional and soft material and are installed to the ends of the limbs.

23. The capsule type micro-robot moving system as claimed in claim 22, wherein the bottoms of the adhesive plates are made of flexible materials and have a plurality of protrusions.

24. The capsule type micro-robot moving system as claimed in claim 22, wherein each of the adhesive plates has a plurality of cilium-shaped protrusions.

25. The capsule type micro-robot moving system as claimed in claim 24, wherein a ratio of a diameter to a height of the protrusions ranged 1:1 to 1:100.

* * * * *